United States Patent
Hopkins

(10) Patent No.: US 10,342,669 B2
(45) Date of Patent: Jul. 9, 2019

(54) CONVERTIBLE GLENOID

(71) Applicant: Zimmer, Inc., Warsaw, IN (US)

(72) Inventor: Andrew Rolfe Hopkins, Winterthur (CH)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 15/564,636

(22) PCT Filed: Apr. 6, 2016

(86) PCT No.: PCT/US2016/026106
§ 371 (c)(1),
(2) Date: Oct. 5, 2017

(87) PCT Pub. No.: WO2016/164385
PCT Pub. Date: Oct. 13, 2016

(65) Prior Publication Data
US 2018/0092747 A1    Apr. 5, 2018

Related U.S. Application Data

(60) Provisional application No. 62/144,031, filed on Apr. 7, 2015.

(51) Int. Cl.
  *A61F 2/40*  (2006.01)
  *A61F 2/30*  (2006.01)
  *A61F 2/46*  (2006.01)

(52) U.S. Cl.
  CPC ...... *A61F 2/4081* (2013.01); *A61F 2002/305* (2013.01); *A61F 2002/30332* (2013.01);
  (Continued)

(58) Field of Classification Search
  CPC .. A61F 2/38; A61F 2002/3863; A61F 2/3872; A61F 2/389; A61F 2002/3895;
  (Continued)

(56) References Cited

U.S. PATENT DOCUMENTS 4,964,865 A * 10/1990 Burkhead ................. A61F 2/40
                                                                     623/19.11
5,080,673 A *  1/1992 Burkhead ................. A61F 2/40
                                                                     623/19.11
(Continued)

FOREIGN PATENT DOCUMENTS

CN       107645942       1/2018
JP       2018515176      6/2018
WO     WO-2016164385 A1  10/2016

OTHER PUBLICATIONS

"International Application Serial No. PCT/US2016/026106, International Search Report dated Aug. 8, 2016", 6 pgs.
(Continued)

*Primary Examiner* — Alvin J Stewart
(74) *Attorney, Agent, or Firm* — Schwegman Lundberg & Woessner, P.A.

(57) ABSTRACT

A glenoid system (100) includes a baseplate (102) configured to attach to a glenoid cavity of a patient. In a primary configuration, a biocompatible plastic liner (332) can snap into a circumferential groove (120) on the baseplate, to attach to a lateral facing surface (104) of the baseplate, at one or more locations around the groove. In a reverse configuration, a glenosphere (544, 644) can attach to an adapter (542, 642), which in turn can attach to the lateral-facing surface of the baseplate. The adapter can introduce lateral and/or angular offsets between the baseplate and the glenosphere, which can correct for unwanted offsets or inclinations. A middle peg extension (752) can screw onto a medial end of the middle peg (114), which can offer different combinations of peg length and peg material. The baseplates can be made available in various discrete sizes, each of which has the same distance between the middle peg and an inferior screw hole (112).

18 Claims, 12 Drawing Sheets

(52) U.S. Cl.
CPC ............... *A61F 2002/30405* (2013.01); *A61F 2002/30607* (2013.01); *A61F 2002/30616* (2013.01); *A61F 2002/30772* (2013.01); *A61F 2002/30822* (2013.01); *A61F 2002/30878* (2013.01); *A61F 2002/30884* (2013.01); *A61F 2002/4085* (2013.01); *A61F 2002/4619* (2013.01)

(58) Field of Classification Search
CPC ............... A61F 2/40; A61F 2002/4088; A61F 2002/4092; A61F 2002/4096; A61F 2/4202
See application file for complete search history.

(56) References Cited

U.S. PATENT DOCUMENTS

| | | | | |
|---|---|---|---|---|
| 5,489,310 | A * | 2/1996 | Mikhail | A61B 17/1684 623/19.11 |
| 5,702,447 | A * | 12/1997 | Walch | A61B 17/809 606/309 |
| 6,228,119 | B1 * | 5/2001 | Ondrla | A61F 2/4081 623/19.11 |
| 6,679,916 | B1 * | 1/2004 | Frankle | A61F 2/4081 623/19.12 |
| 6,969,407 | B2 * | 11/2005 | Klotz | A61F 2/4261 623/21.12 |
| 8,632,598 | B2 | 1/2014 | McDaniel et al. | |
| 8,690,951 | B2 * | 4/2014 | Baum | A61F 2/4081 623/18.11 |
| 8,721,728 | B2 * | 5/2014 | Winslow | A61F 2/4081 623/19.12 |
| 9,078,758 | B2 * | 7/2015 | Leibel | A61F 2/4261 |
| 9,345,581 | B2 * | 5/2016 | Winslow | A61F 2/4081 |
| 9,629,725 | B2 * | 4/2017 | Gargac | A61F 2/4081 |
| 2004/0064073 | A1 * | 4/2004 | Heldreth | A61B 5/103 600/595 |
| 2004/0220673 | A1 * | 11/2004 | Pria | A61F 2/40 623/19.12 |
| 2007/0142917 | A1 * | 6/2007 | Roche | A61F 2/4081 623/19.11 |
| 2007/0173945 | A1 * | 7/2007 | Wiley | A61F 2/30734 623/19.13 |
| 2007/0219638 | A1 * | 9/2007 | Jones | A61F 2/4081 623/19.11 |
| 2007/0244563 | A1 * | 10/2007 | Roche | A61F 2/40 623/19.12 |
| 2008/0228281 | A1 * | 9/2008 | Forrer | A61F 2/4014 623/19.12 |
| 2009/0149961 | A1 * | 6/2009 | Dallmann | A61F 2/4003 623/19.11 |
| 2010/0234959 | A1 * | 9/2010 | Roche | A61F 2/40 623/19.13 |
| 2010/0249938 | A1 | 9/2010 | Gunther et al. | |
| 2010/0324691 | A1 * | 12/2010 | Brunnarius | A61F 2/4081 623/19.11 |
| 2012/0253467 | A1 * | 10/2012 | Frankle | A61F 2/40 623/19.11 |
| 2013/0282129 | A1 * | 10/2013 | Phipps | A61F 2/4081 623/19.11 |
| 2014/0025173 | A1 * | 1/2014 | Cardon | A61F 2/4081 623/19.13 |
| 2014/0100664 | A1 * | 4/2014 | Leibel | A61F 2/4261 623/21.13 |
| 2014/0236308 | A1 * | 8/2014 | Oosthuizen | A61F 2/389 623/20.28 |
| 2015/0142122 | A1 * | 5/2015 | Bickley | A61F 2/4081 623/19.11 |
| 2016/0374815 | A1 * | 12/2016 | Siccardi | A61F 2/40 623/19.12 |
| 2017/0056187 | A1 * | 3/2017 | Humphrey | A61F 2/4014 |

OTHER PUBLICATIONS

"International Application Serial No. PCT/US2016/026106, Written Opinion dated Aug. 8, 2016", 6 pgs.
"European Application Serial No. 16716434.2, Response filed Jul. 25, 2018 to Office Action dated Jan. 25, 2018", 21 pgs.
"Chinese Application Serial No. 201680029464.2, Office Action dated Oct. 15, 2018", (W/ English Translation), 13 pgs.
Guo, Xiurong, "Plastic and its processing technology", Material technology and creative design, (Nov. 30, 2014), 14 pgs.
"Chinese Application Serial No. 201680029464.2, Response Filed Jan. 11, 2019 to Office Action dated Oct. 15, 2018", w English Claims, 10 pgs.

* cited by examiner

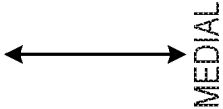
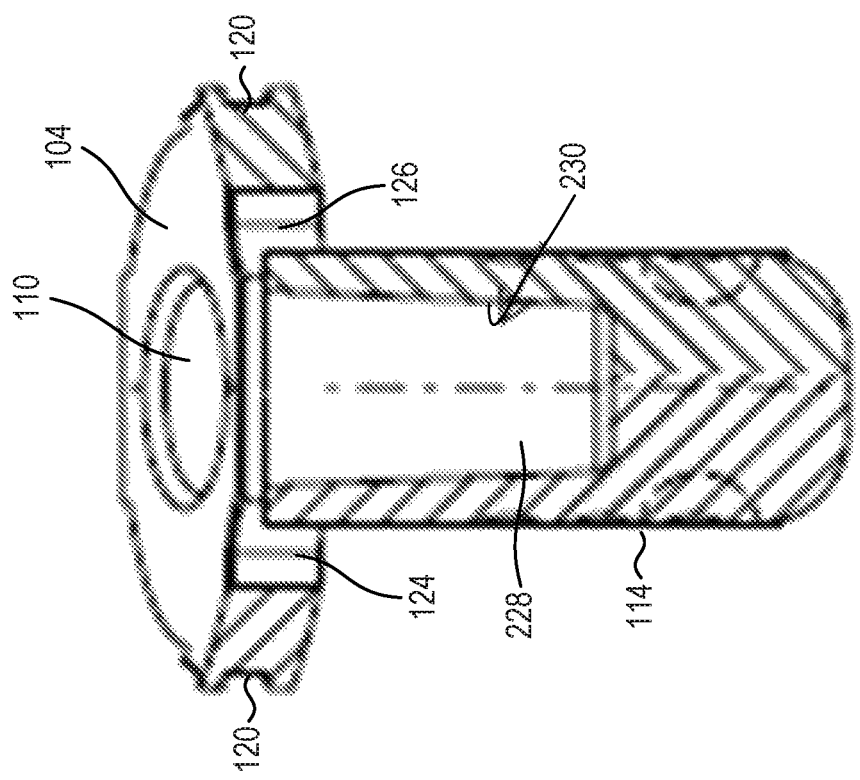
FIG. 2

CONVERTIBLE GLENOID

CROSS-REFERENCE TO RELATED APPLICATION

This application is a U.S. National Stage Application under 35 U.S.C. 371 of International Application Serial No. PCT/US2016/026106, filed Apr. 6, 2016, which published as WO2016/164385A1 on Oct. 13, 2016, which claims the benefit of U.S. Provisional Application No. 62/144,031, titled "Convertible Glenoid", filed Apr. 7, 2015, the entirety of each of which are hereby incorporated by reference.

BACKGROUND

Shoulder arthroplasty is a surgical procedure in which all or part of the glenohumeral joint is replaced by one or more prosthetic implants. Frequently, shoulder arthroplasty is performed to relieve pain due to severe arthritis or severe joint damage. There is ongoing effort to improve the prosthetic components utilized in this surgical procedure.

OVERVIEW

In a natural glenohumeral (shoulder) joint, the glenoid cavity of the scapula (shoulder blade) is concavely curved. The head of the humerus (upper arm bone) is convexly curved, is held against the glenoid cavity, and can pivot in two dimensions around its center of curvature.

A prosthetic shoulder system can include elements that retain the same concavity of the natural joint. For instance, a prosthetic shoulder system can include a glenoid component attachable to the scapula and having a concave surface, and a humeral component attachable to the humerus and having a convex surface. Such a configuration is known as a primary configuration.

Alternatively, the prosthetic shoulder system can include implant components that have the opposite concavity of the natural joint. For instance, the glenoid component can include a convex surface, attachable to the scapula, and the humeral component can include a concave surface, attachable to the humerus. Such a configuration is known as a reverse configuration. The reverse configuration can benefit patients with damaged rotator cuffs or other muscle deterioration.

A glenoid component that can accommodate both the primary configuration and the reverse configuration is known as a convertible glenoid. In some examples, convertible glenoids can provide more flexibility for a practitioner during surgery than glenoids dedicated to primary or reverse configurations. In some cases, a convertible glenoid can reduce a number of inventory parts needed to perform a shoulder surgery.

Any or all of the features described in this Overview can be used independently, or used together in any suitable combination. This Overview is intended to provide examples of the present patent document. It is not intended to provide an exclusive or exhaustive explanation of the invention. The Detailed Description below is included to provide further information about the present convertible glenoid.

BRIEF DESCRIPTION OF THE DRAWINGS

In the drawings, which are not necessarily drawn to scale, like numerals describe similar components in different views. The drawings illustrate generally, by way of example, but not by way of limitation, various embodiments discussed in the present patent document.

FIG. 2 shows a cross-section of the baseplate and middle peg from FIGS. 1A-B, in accordance with some embodiments.

DETAILED DESCRIPTION

Figure 1:
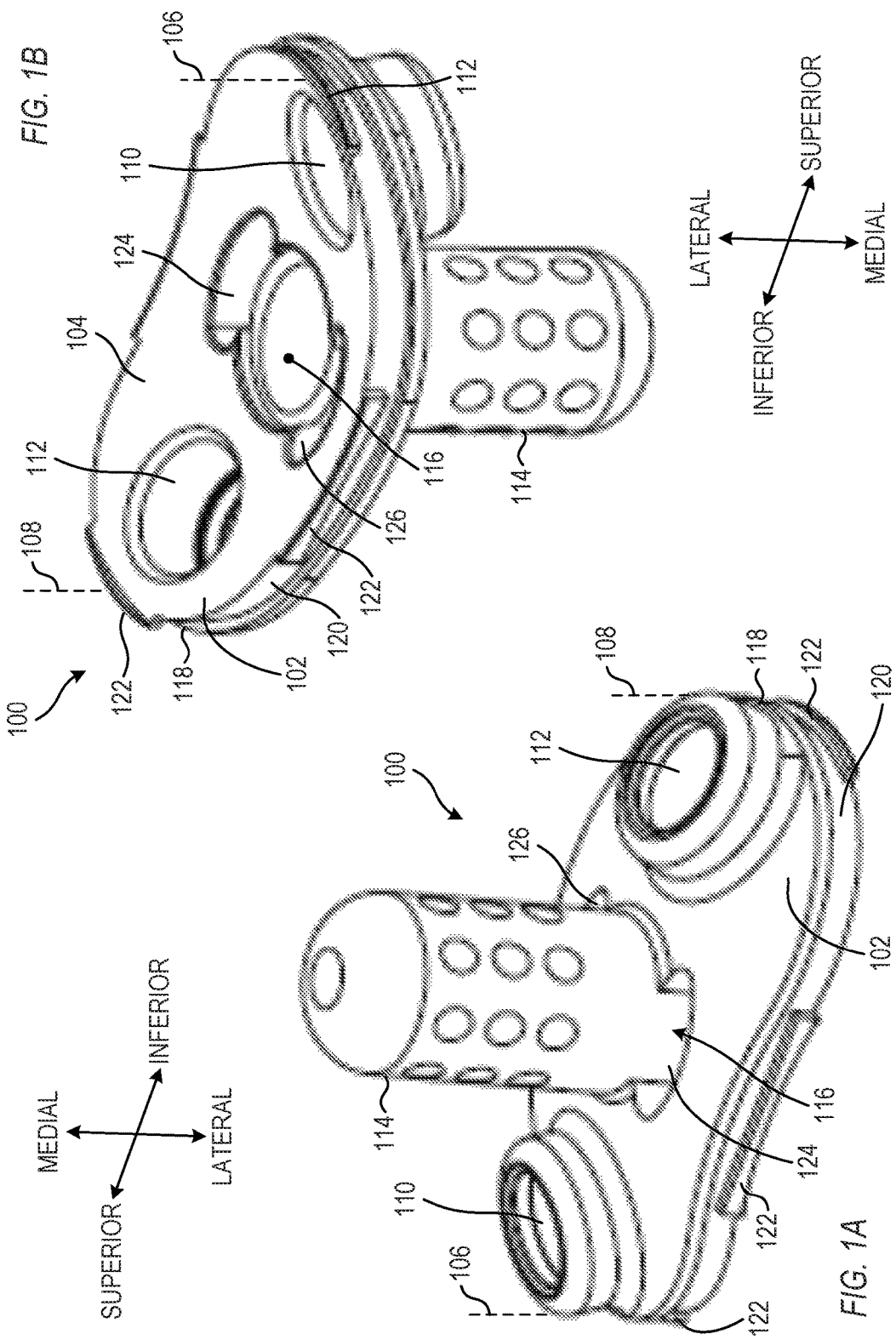
FIGS. 1A-B show two views of an example of a glenoid system, in accordance with some embodiments.

In the following Detailed Description, the terms lateral, medial, superior, and inferior are used to describe the relative orientations of particular elements and features. It will be understood that these terms are used merely for convenience, and describe the relative orientations when the glenoid system is surgically implanted in a shoulder of a patient. For instance, a surface may be described herein as a lateral-facing surface, because such a surface may face a lateral direction when the glenoid system is implanted. One of ordinary skill in the art will readily appreciate that the term lateral-facing surface can be used to describe the orientation of such a surface, even when such a surface has not been surgically implanted. As such, the terms lateral, medial, superior, and inferior can all be considered to be precise modifiers, which can describe elements or features that have not, or not yet, been surgically implanted.

A glenoid system can include a metallic baseplate configured to attach to a glenoid cavity of a patient. The baseplate can be configured to operate in either a primary configuration (e.g., the same concavity of the natural shoulder) or a reverse configuration (e.g., the opposite concavity of the natural shoulder).

In the primary configuration, a biocompatible plastic liner can snap into a circumferential groove on the baseplate, to attach to a lateral-facing surface of the baseplate, at one or more locations around the groove. Attaching the plastic liner via snapping into the circumferential groove on the baseplate can be more effective than other attachment techniques, which can sometimes lead to disassociation of the plastic liner, overstuffing, or loosening of the implanted baseplate. In some examples, using a plastic liner attached to a metal baseplate can be more durable than using a purely plastic baseplate.

In the reverse configuration, a glenosphere or glenoid shield can attach via taper fit to an adapter, which in turn can attach via taper fit to the lateral-facing surface of the baseplate. The adapter can have a lateral and/or angular offset between the taper elements, so that the adapter can controllably introduce lateral and/or angular offsets between the baseplate and the glenosphere, or between the baseplate and the glenoid shield. As such, the adapter can correct for unwanted offsets or inclinations of the glenosphere or glenoid shield.

A middle peg can extend medially from the baseplate. An optional middle peg extension can screw onto a medial end of the middle peg. The middle peg extensions can be made available in different combinations of length and material. Using a system or kit of modular middle pegs can be smaller and less expensive than using a comparable system or kit of glenoid baseplates that have integral middle pegs.

The baseplates can be made available in various discrete inferior-to-superior sizes, each of which has the same distance between the middle peg and an inferior screw hole. Using such a system or kit can increase the spacing between the inferior and superior screws for a particular anatomical size of the patient, which can increase stability of the baseplate during use. Using such a system or kit can also allow additional elements to use a standardized spacing between the middle peg and inferior screw hole, regardless of anatomical size.

In some examples, the glenoid baseplate can define one or more cut-outs extending through the baseplate and shaped to accommodate an instrument to relieve bone ongrowth or ingrowth. In some examples, the cut-outs can be concentric with the middle peg. The cut-outs can be used for revision surgery, and need not be used during initial implantation.

The baseplate, circumferential groove, liner, adapter, glenosphere, middle peg, and middle peg extension are shown in FIGS. 1-11, and are described in detail below.

FIGS. 1A-B show two views of an example of a glenoid system 100, in accordance with some embodiments. Glenoid system 100 is but one example of a glenoid system; other suitable glenoid systems can also be used.

Glenoid system 100 can include a baseplate 102 that can attach to a glenoid cavity (e.g., on the lateral face of the scapula) of a patient. In some examples, baseplate 102 can be formed from a biocompatible metal or a biocompatible metal alloy, such as titanium or a cobalt-chrome alloy. In some examples, one or more portions of the baseplate 102 that can contact bone can be treated to improve fixation to the bone. Examples of suitable fixation treatments can include surface blasting, hydroxyapatite coating (HAC), plasma spray, and others.

Baseplate 102 can define a lateral-facing surface 104. Lateral-facing surface 104 can face laterally and can extend from a superior end 106 of the baseplate 102 to an inferior end 108 of the baseplate 102 when the baseplate 102 is attached to the glenoid cavity. In some examples, the lateral-facing surface 104 can be concave. In other examples, the lateral-facing surface 104 can be convex.

Baseplate 102 can define a superior hole 110 through the lateral-facing surface 104 proximate the superior end 106 of the baseplate 102. Baseplate 102 can define an inferior hole 112 through the lateral-facing surface 104 proximate the inferior end 108 of the baseplate 102. During surgery, a practitioner can screw the baseplate 102 to the glenoid cavity, with screws that extend through the superior hole 110 and the inferior hole 112 in the baseplate 102. In general, it is desirable to position the superior hole 110 and the inferior hole 112 as far apart as is practical, which can stabilize the fixation of the baseplate 102 to the glenoid cavity. In some examples, one or both of the superior hole 110 and inferior hole 112 are countersunk, so that when the practitioner fully engages a screw through the respective hole, the head of the screw lies below (e.g., medial to) the lateral-facing surface 104. In some examples, the screw can be poly-axial.

Baseplate 102 can be coupled to a middle peg 114 at a middle area 116 between the superior hole 110 and the inferior hole 112. The middle peg 114 can extend medially from the baseplate 102 when the baseplate 102 is attached to the glenoid cavity. Over time, bone can grow on and around the middle peg 114, which can fixate the implanted baseplate 102. In some examples, the middle peg 114 can be shaped to enhance fixation to the bone. For instance, the middle peg 114 can have a generally cylindrical shape, with fins, dimples, depressions, or other features that engage bone that grows around the middle peg 114. In some examples, one or more portions of the middle peg 114 can be treated to improve fixation to the bone. Examples of suitable fixation treatments can include surface blasting, hydroxyapatite coating (HAC), plasma spray, and others.

In some examples, baseplate 102 can define a circumferential edge 118 around the lateral-facing surface 104. In some examples, the circumferential edge 118 can have an elongated, oval, or pear-shaped footprint, when viewed end-on from the medial or lateral direction. In other examples, the circumferential edge 118 can have another suitably shaped footprint.

In some examples, the circumferential edge 118 can define a circumferential groove 120 therein. The circumferential groove 120 can be used to attach one or more additional elements to the baseplate 102. For instance, a biocompatible plastic liner can have one or more mating features that snap into all or a portion of the circumferential groove 120, thereby attaching the biocompatible plastic liner to the baseplate 102. As another example, during surgery, the circumferential groove 120 can support removable attachment of one or more trial components. Other suitable components can also snap into the circumferential groove 120, as needed.

In some examples, baseplate 102 can further include one or more overhang elements 122. Overhang elements 122 can extend medially from respective locations along the circumference of the lateral-facing surface 104. Overhang elements 122 can form a lip with the circumferential groove 120, so that once an element has snapped into the circumferential groove 120, the overhang elements 122 block the element from being radially extended outward, out of the circumferential groove 120. In some examples, overhang elements 122 are located at discrete locations around the circumference of the lateral-facing surface 104, such as at four equally-spaced locations around the circumference.

Baseplate 102 can optionally include one or more features that are beneficial during revision surgery, e.g., surgery to remove an implanted baseplate 102. For instance, baseplate 102 can include one or more slots, holes, or apertures around the middle peg 114 that allow a practitioner to insert and/or circumferentially turn a tool around the middle peg 114 to dissociate any bone growth from the middle peg 114.

In some examples, baseplate 102 can further define a first slot 124 through the lateral-facing surface 104. First slot 124 can be elongated circumferentially around the middle area 116 and adjacent to the middle peg 114. In some examples, first slot 124 can have an inner edge coincident with a portion of an outer edge of the middle peg 114. In some examples, first slot 124 can extend less than halfway around the middle peg 114. In some examples, first slot 124 can be shaped and sized to accommodate an instrument to relieve bone ongrowth or ingrowth on the middle peg.

In some examples, baseplate 102 can further define a second slot 126 through the lateral-facing surface 104. Second slot 126 can be elongated circumferentially around the middle area 116 and adjacent to the middle peg 114. In some examples, second slot 126 can extend less than halfway around the middle peg 114. In some examples, second slot 126 can be diametrically opposed to first slot 124. In some examples, first slot 124 and second slot 126 can be shaped and sized to accommodate an instrument to relieve bone ongrowth or ingrowth on the middle peg 114. Slots 124, 126 are but one example of holes or apertures that can accommodate a bone-dissociating tool. In some examples, baseplate 102 can define more than two slots.

The circumferential groove 120, the overhang elements 122, the first slot 124, and the second slot 126 can all be used singly on a baseplate 102, all together on a baseplate 102, or in any combination with one another on a baseplate 102.

FIG. 2 shows a cross-section of the baseplate 102 and middle peg 114 from FIGS. 1A-B, in accordance with some embodiments. In FIG. 2, the superior direction is into the plane of the page, and the inferior direction is out of the plane of the page. FIG. 2 shows portions of the lateral-facing surface 104, the circumferential groove 120, the first slot 124 and the second slot 126. FIG. 2 also shows a portion of the superior hole 110, disposed behind the middle peg 114 in the view of FIG. 2.

Additionally, FIG. 2 shows a recess 228 in the middle peg 114. In some examples, the recess 228 can have a female taper 230. In some examples, the female taper 230 can be elongated in one direction, compared to a perpendicular direction. For instance, the female taper 230 can be elongated along the inferior-superior direction, compared to a direction perpendicular to the inferior-superior direction. In other examples, the female taper 230 can be rotationally symmetric. Recess 228 can serve two functions, related to additional elements described below.

First, for surgeries requiring the primary configuration, the recess 228 can act as a guide for a centering feature on a biocompatible plastic liner attachable to the baseplate 102. In some examples, the centering feature can have an elongated cross-section that matches the elongation of the female taper 230. As the biocompatible plastic liner is brought into position, the elongations can ensure that the biocompatible plastic liner is azimuthally aligned with the baseplate 102. The recess 228 does not form a taper fit with the centering feature. The biocompatible plastic liner and centering feature are shown in FIGS. 3A-B and 4, and are described in detail below.

Figure 5:
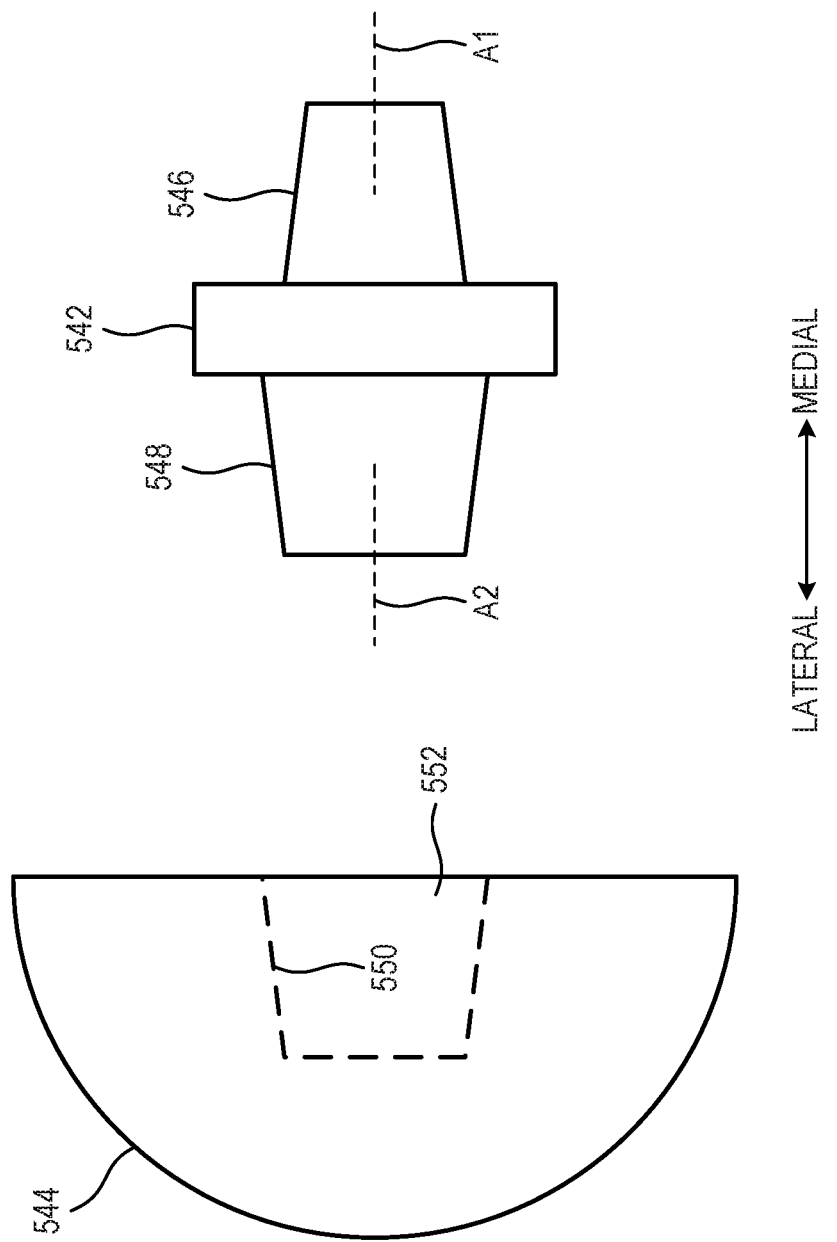
FIG. 5 shows a side view of an example of an adapter which can attach a glenosphere or glenoid shield to a baseplate, in accordance with some embodiments.
Figure 6:
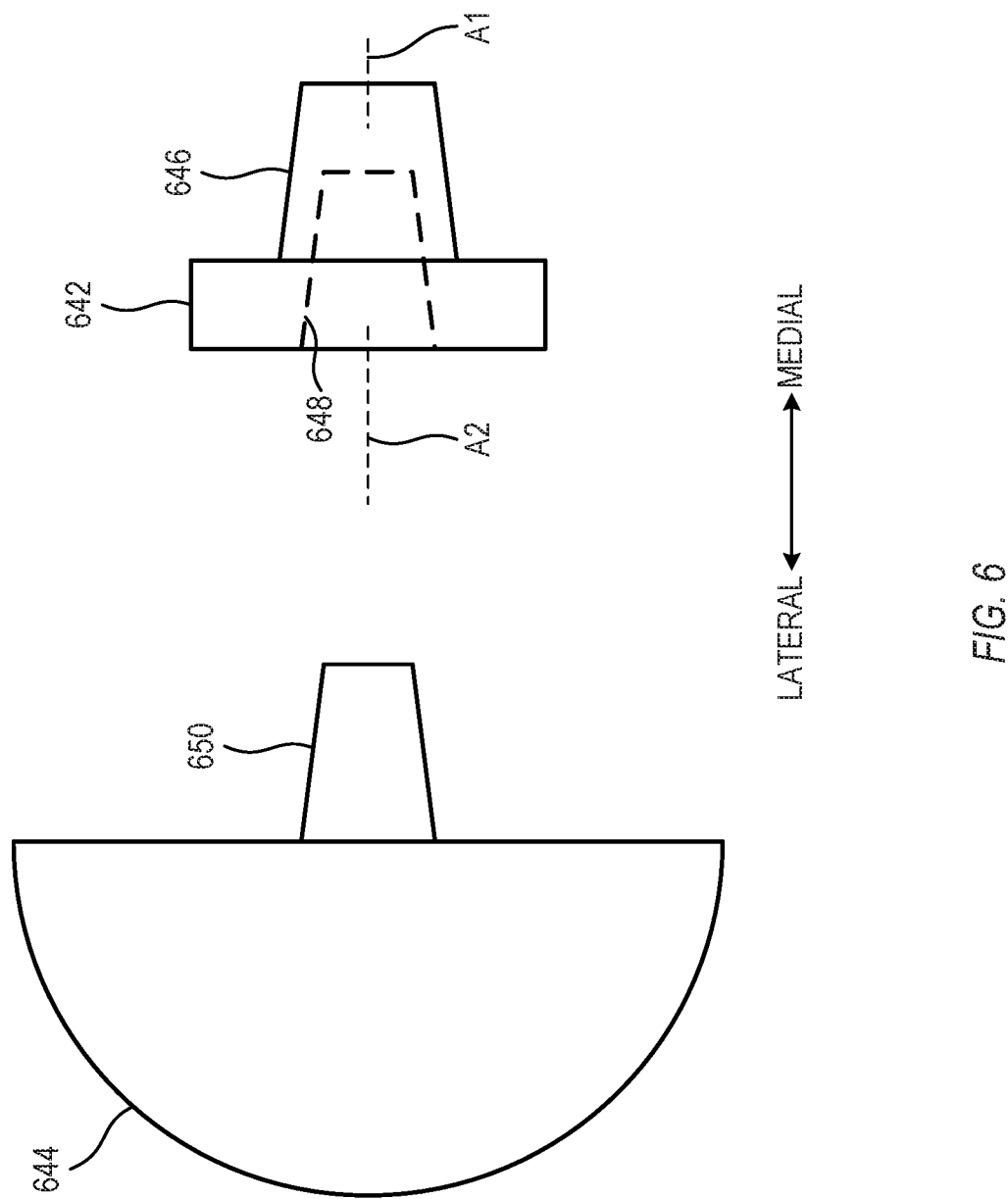
FIG. 6 shows a side view of another example of an adapter which can attach a glenosphere or glenoid shield to a baseplate, in accordance with some embodiments.

Second, for surgeries requiring the reverse configuration, the recess 228 can form a taper fit with an adapter, which in turn attaches to a glenosphere or a glenoid shield via another taper fit. The tapers on the adapter secure the adapter to the baseplate 102 and middle peg 114, and also secure the adapter to the glenosphere or a glenoid shield. The tapers on the adapter can be linearly and/or angularly offset with respect to one another, so that the adapter can correct for at least one of medio-lateral offset, supero-inferior offset, inclination, and retroversion between the baseplate 102 and the glenosphere or glenoid shield. The adapter is shown in FIGS. 5 and 6, and is described in detail below.

Figure 3A:
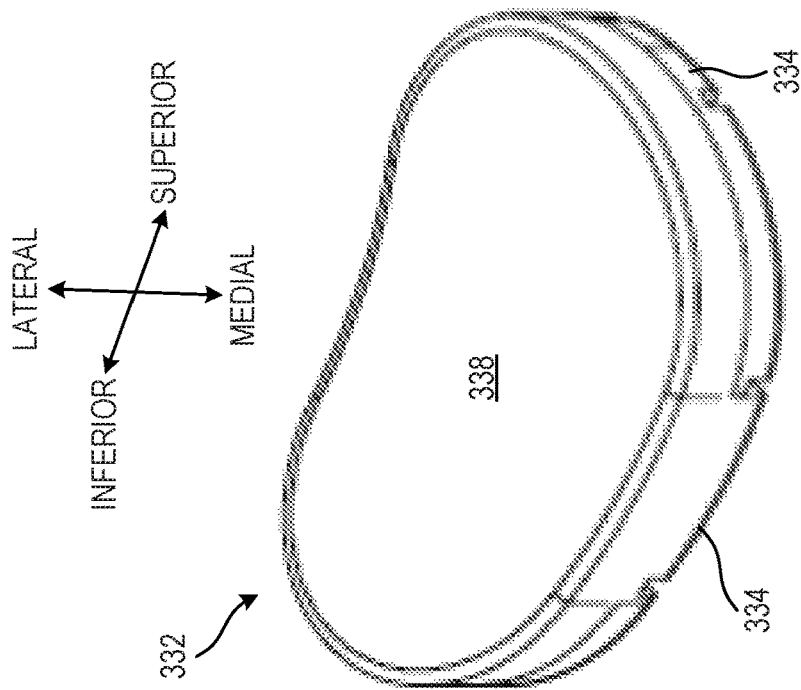
FIGS. 3A-B show two views of an example of a liner, in accordance with some embodiments.
Figure 3B:
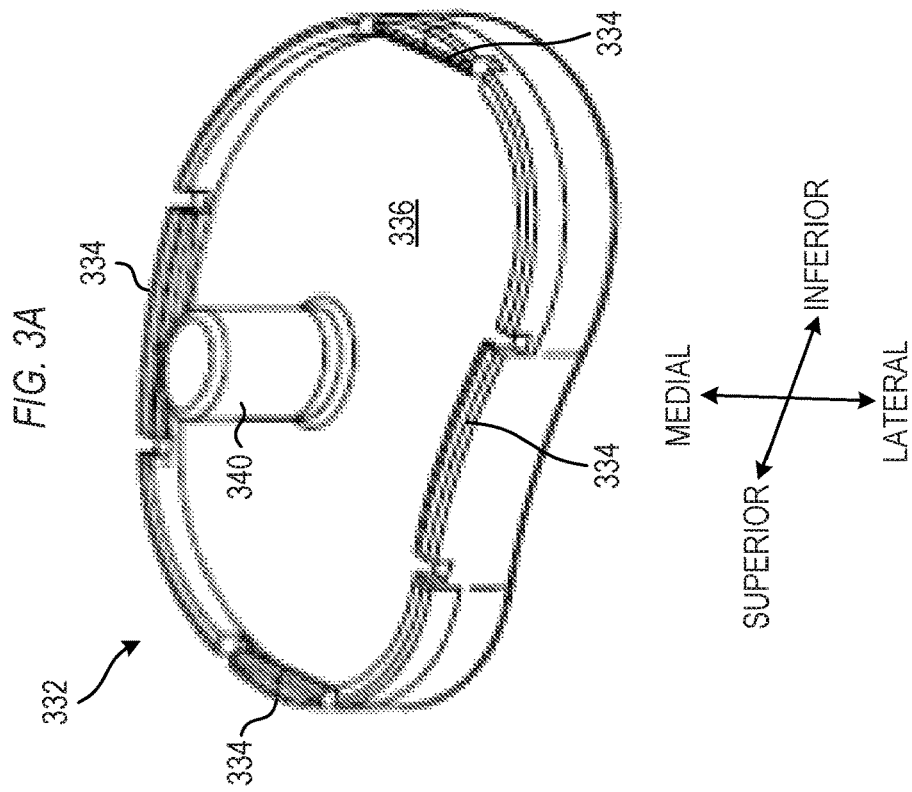
Figure 4:
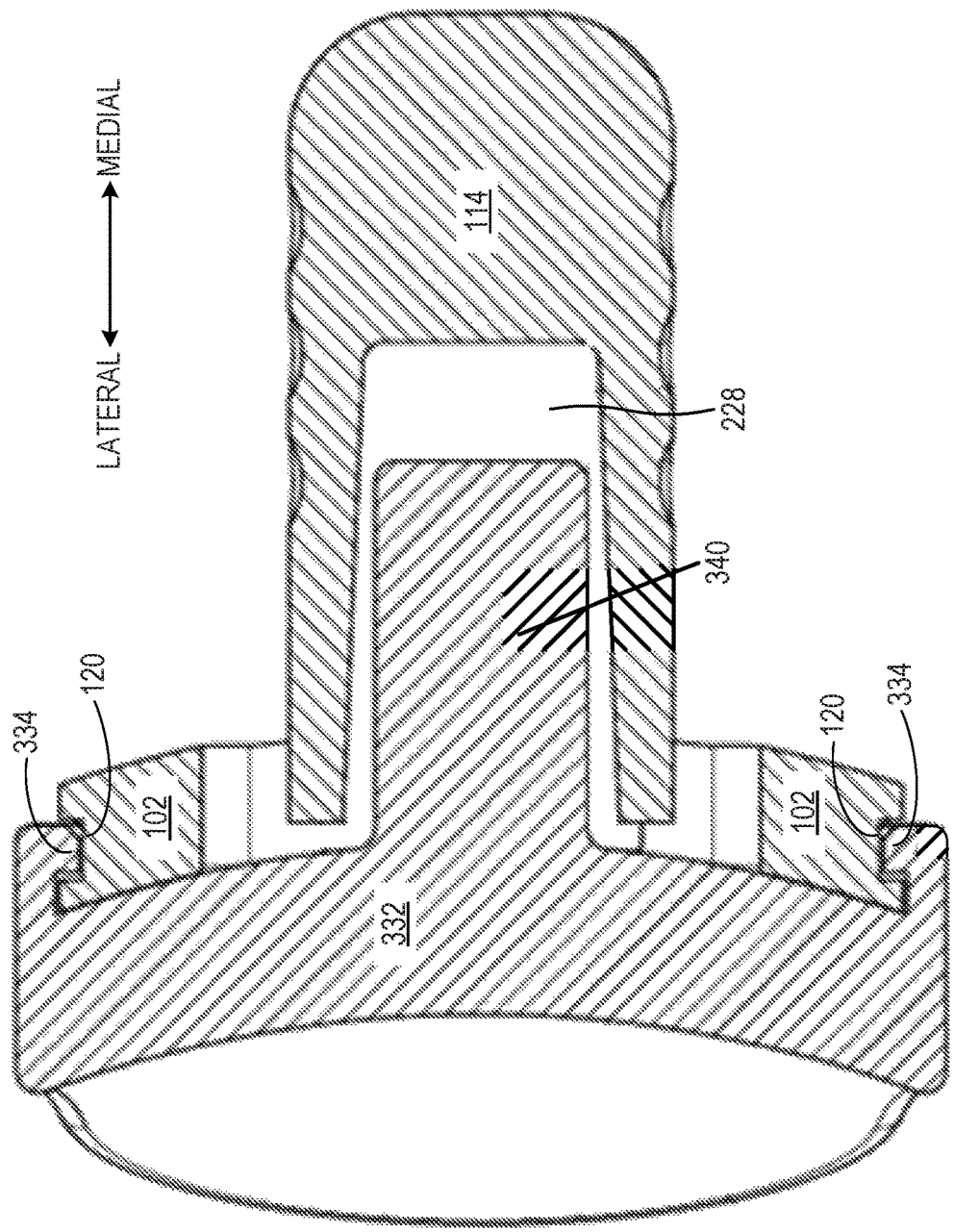
FIG. 4 shows a cross-section of the liner of FIG. 3, attached to the baseplate of FIGS. 1A-B.

FIGS. 3A-B show two views of an example of a liner 332, in accordance with some embodiments. Liner 332 can be formed from a biocompatible plastic material, such as polyethylene, polyphenylsulfone (PPSU), polyoxymethylene (POM), and others. Liner 332 is but one example of a biocompatible plastic liner; other suitable liners can also be used.

In some examples, liner 332 can be shaped to snap into the circumferential groove of the baseplate and thereby attach to the baseplate. In some examples, when the liner 332 is attached to the baseplate, the liner 332 can fully surround a lateral end of the baseplate, including all or a portion of a circumferential edge of the baseplate.

In some examples, liner 332 can include a flexible raised lip 334 around at least a portion of its circumference. The flexible raised lip 334 can deflect radially outward, engage the circumferential groove, and retract radially into the circumferential groove when the liner 332 is forced against the baseplate.

In some examples, liner 332 can include a smooth face 336 facing the baseplate, and a smooth face 338 facing away from the baseplate. Once implanted in a patient, smooth face 338 movably contacts a convex surface on a corresponding element attached to the humerus, which forms the artificial shoulder joint. The convex surface is typically metallic, so that the interface at smooth face 338 is between metal and plastic, and not between metal and metal.

In some examples, liner 332 can include a centering feature 340. Centering feature 340 can be made integrally with the liner 332, or made separately from the liner and attached to the liner 332. The centering feature 332 can extend medially through the baseplate, and extend medially into recess 228 (FIG. 2) of the middle peg, when the liner 332 is attached to the baseplate. As described above, the centering feature 340 can have an elongated cross-section that matches the elongation of the female taper 230 (FIG. 2). As the liner 332 is brought into position, the elongations can ensure that the liner 332 is azimuthally aligned with the baseplate. In some examples, the centering feature 340 does not form a taper fit within the recess, and does not mechanically support the liner 332.

FIG. 4 shows a cross-section of the liner 332 of FIG. 3, attached to the baseplate 102 of FIGS. 1A-B. In the example of FIG. 4, the flexible raised lip 334 on the liner 332 can engage the circumferential groove 120 on the baseplate 102. In the example of FIG. 4, the centering feature 340 can enter into the recess 228 in the middle peg 114, which is coupled to the baseplate 102. In the example of FIG. 4, the centering feature 340 can have minimal or no contact with the wall of the recess 228. In some examples, in the event of a disassociation, this geometry can allow a series of radiological spheres to be placed to support identification of the liner in the joint space.

The liners of FIGS. 3 and 4 can be used in the primary configuration singly, or in any suitable combination with any or all of the other features discussed herein, such as the circumferential groove 120 (FIG. 1), the overhang elements 122 (FIG. 1), the first slot 124 (FIG. 1), and the second slot 126 (FIG. 1).

FIG. 5 shows a side view of an example of an adapter 542 which can attach a glenosphere 544 to a baseplate, in accordance with some embodiments. Adapter 542 can be formed from a biocompatible material, such as a titanium alloy, or other suitable biocompatible metal or a biocompatible metal alloy. FIG. 5 is but one example of an adapter 542; other suitable adapters can also be used.

Adapter 542 can have a first taper 546. The first taper 546 can be a male taper sized and shaped to form a taper fit with the recess, such as recess 228 (FIG. 2) in the middle peg (FIGS. 1 and 2). The first taper 546 can be centered around a first axis (A1).

Adapter 542 can have a second taper 548. The second taper 548 can be sized and shaped to form a taper fit with a glenosphere or a glenoid shield. In the example of FIG. 5, the second taper 548 is a male taper, which is sized and shaped to form a taper fit with a female taper 550 inside a recess 552 of the glenosphere 544. The second taper 548 can be centered around a second axis (A2).

In some examples, the second axis (A2) can be linearly offset from the first axis (A1). In some examples, the second axis (A2) can be angularly offset from the first axis (A1). In some examples, the second axis (A2) can be both linearly offset and angularly offset from the first axis (A1). Such an offset can correct for at least one of medio-lateral offset, supero-inferior offset, inclination, and retroversion between the baseplate and the glenosphere or glenoid shield.

FIG. 6 shows a side view of another example of an adapter 642 which can attach a glenosphere 644 to a baseplate, in accordance with some embodiments. Compared with the example of FIG. 5, the second taper 648 and corresponding taper 650 on the glenosphere have reversed genders. FIG. 6 is but one example of an adapter 642; other suitable adapters can also be used.

Adapter 642 can have a first taper 646, which can be a male taper sized and shaped to form a taper fit with the recess in the middle peg. The first taper 646 can be centered around a first axis (A1).

Adapter 642 can have a second taper 648. The second taper 648 can be sized and shaped to form a taper fit with a glenosphere or a glenoid shield. In the example of FIG. 6, the second taper 648 is a female taper, which is sized and shaped to form a taper fit with a male taper 650 on the glenosphere 644. The second taper 648 can be centered around a second axis (A2). The second axis (A2) can be linearly and/or angularly offset from the first axis (A1).

The glenosphere 644 of FIG. 6 may be referred to as a monoblock glenosphere. Using the adapter 642 to connect the monoblock glenosphere to the baseplate has advantages over connecting the monoblock glenosphere directly to the baseplate, such as being able to correct for at least one of medio-lateral offset, supero-inferior offset, inclination, and retroversion between the baseplate and the glenosphere or glenoid shield.

The adapters of FIGS. 5 and 6 can be used in the reverse configuration singly, or in any suitable combination with any or all of the other features discussed herein, such as the circumferential groove 120 (FIG. 1), the overhang elements 122 (FIG. 1), the first slot 124 (FIG. 1), and the second slot 126 (FIG. 1).

Figure 7:
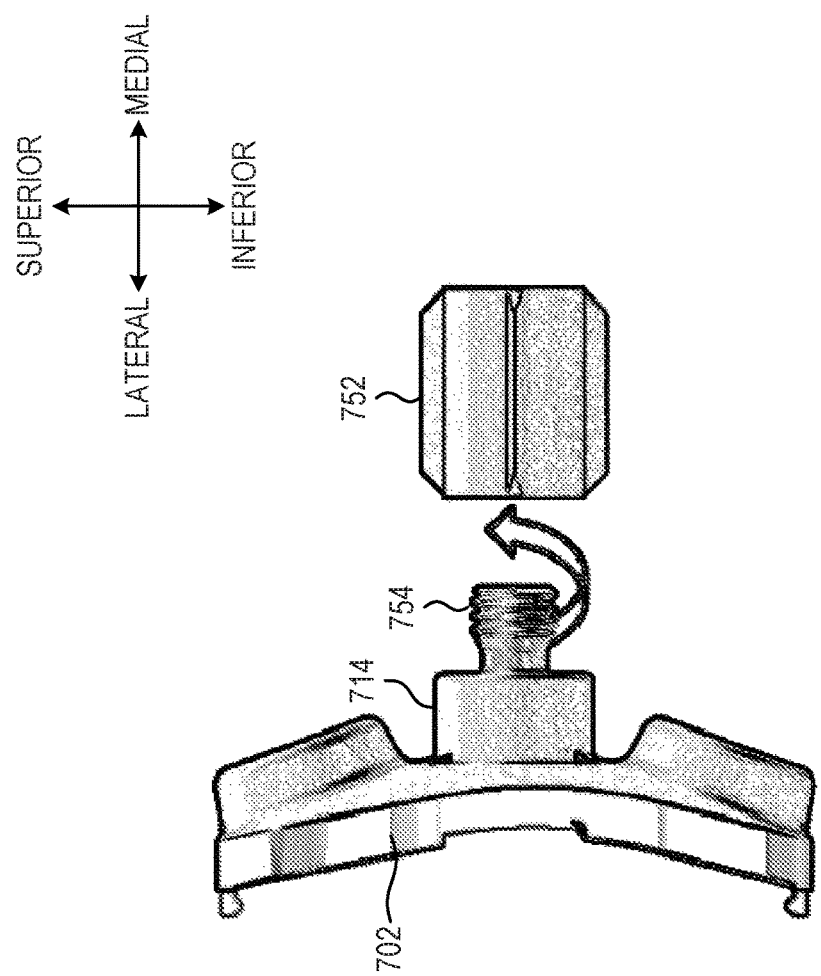
FIG. 7 shows a side view of an example of a baseplate coupled to a middle peg, where the middle peg is configured to attach to a middle peg extension, in accordance with some embodiments.

FIG. 7 shows a side view of an example of a baseplate 702 coupled to a middle peg 714, where the middle peg 714 is configured to attach to a middle peg extension 752, in accordance with some embodiments. The middle peg extension 752 can medially extend the middle peg 714.

In some examples, the middle peg extension 752 can be formed from biocompatible metal or a biocompatible metal alloy, such as titanium or a cobalt-chrome alloy. In some examples, the middle peg extension 752 can have a circular cross-section (e.g., the cross-section, taken in a plane perpendicular to the lateral-medial direction, can be rotationally symmetric with respect to a lateral-medial axis). In some examples, the middle peg extension 752 can have features that can encourage bone ongrowth, such as fins, dimples, and the like. In some examples, one or more portions of the middle peg extension 752 can be treated to improve fixation to the bone. Examples of suitable fixation treatments can include surface blasting, hydroxyapatite coating (HAC), plasma spray, and others. In some examples, Trabecular Metal can be used to enhance fixation.

In some examples, a lateral end of the middle peg extension 752 can have male or female threads that mate with corresponding female or male threads 754 at a medial end of the middle peg 714. In other examples, a lateral end of the middle peg extension 752 can have a male or female taper that can form a taper fit with a corresponding female or male taper at a medial end of the middle peg 714.

Extending the middle peg 714 with an attachable middle peg extension 752 can allow greater flexibility in selecting a configuration for the area of the extension that contacts bone. For instance, in some examples, the middle peg extension 752 can be selected from a plurality of middle peg extensions. The plurality of middle peg extensions can be made available as a kit, a system, or a collection of middle peg extensions. In some examples, each middle peg extension in the plurality can have a unique combination of length and material. In some examples, a practitioner can select a suitable length, from the discrete lengths available in the plurality of middle peg extensions, to best match an anatomy of the patient.

A threaded or taper-fit middle peg extension, such as 752, can be used singly or in any suitable combination with any or all of the other features discussed herein, such as the circumferential groove 120 (FIG. 1), the overhang elements 122 (FIG. 1), the first slot 124 (FIG. 1), the second slot 126 (FIG. 1), the centering feature 340 extending into the recess 228 of the middle peg 114 (FIG. 4), and the adapters 542, 642 (FIGS. 5 and 6).

Figure 8:
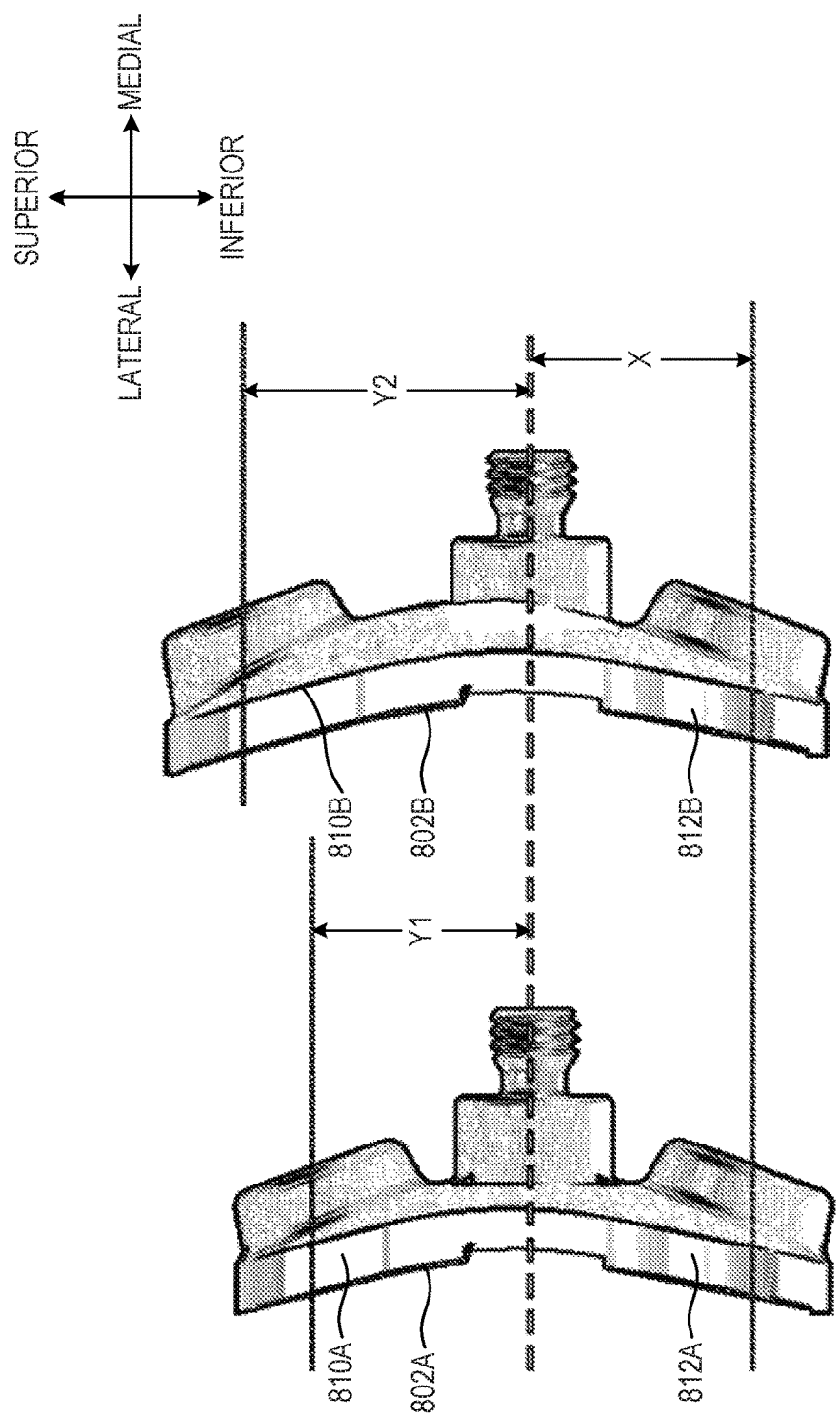
FIG. 8 shows a side view of an example of a plurality of baseplates, in accordance with some embodiments.

FIG. 8 shows a side view of an example of a plurality of baseplates 802A-B, in accordance with some embodiments. Each baseplate 802A-B in the plurality can have the same spacing (X) between the middle area 818A-B and the inferior hole 812A-B. In some examples, the spacings are denoted from a center of the inferior holes 812A-B to a center of the middle peg 814A-B. Each baseplate 802A-B in the plurality can having a unique spacing (Y1, Y2) between the middle area 818A-B and the superior hole 810A-B. In some examples, the spacings are denoted from a center of the superior holes 810A-B to the center of the middle peg 814A-B. In some examples, the baseplates 802A-B in the plurality can be made available as a kit, a system, or a collection of baseplates 802A-B.

A practitioner can select a baseplate 802A-B having an inferior-to-superior size matched to an anatomy of the patient. For a given baseplate size, the inferior holes 812A-B and the superior holes 810A-B can be spaced as far apart as is practical, which can increase stability of the baseplate 802A-B when the baseplate 802A-B is attached to the glenoid cavity. In addition, the constant spacing between the inferior holes 812A-B and the middle area 818A-B can help ensure that a glenosphere is positioned consistently, regardless of a size of the baseplate 802A-B.

The differently-sized baseplates shown in FIG. 8 can be used singly or in any suitable combination with any or all of the other features discussed herein, such as the circumferential groove 120 (FIG. 1), the overhang elements 122 (FIG. 1), the first slot 124 (FIG. 1), the second slot 126 (FIG. 1), the centering feature 340 extending into the recess 228 of the middle peg 114 (FIG. 4), the adapters 542, 642 (FIGS. 5 and 6), and the threaded or taper-fit middle peg extension 752 (FIG. 7).

Figure 9:
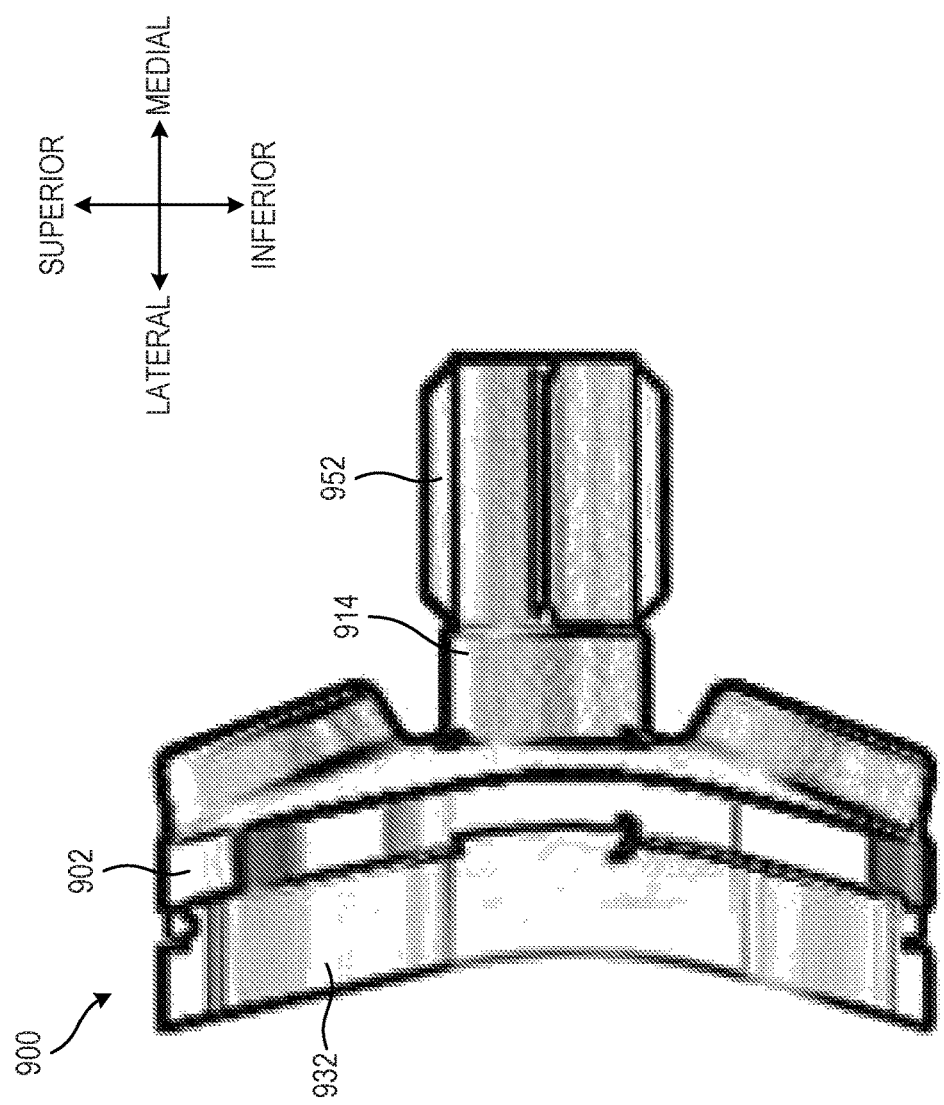
FIG. 9 shows a side view of an example of a glenoid system in the primary configuration, in accordance with some embodiments.

FIG. 9 shows a side view of an example of a glenoid system 900 in the primary configuration, in accordance with some embodiments. Glenoid system 900 can include a baseplate 902, a liner 932 configured to be snapped onto a lateral side of the baseplate 902, a middle peg 914 extending medially from the baseplate 902, and an optional middle peg extension 952 configured to be screwed onto a medial end of the middle peg 914. Liner 932 can be attached using the circumferential groove 120 (FIG. 1), or with another suitable attachment mechanism.

Figure 10:
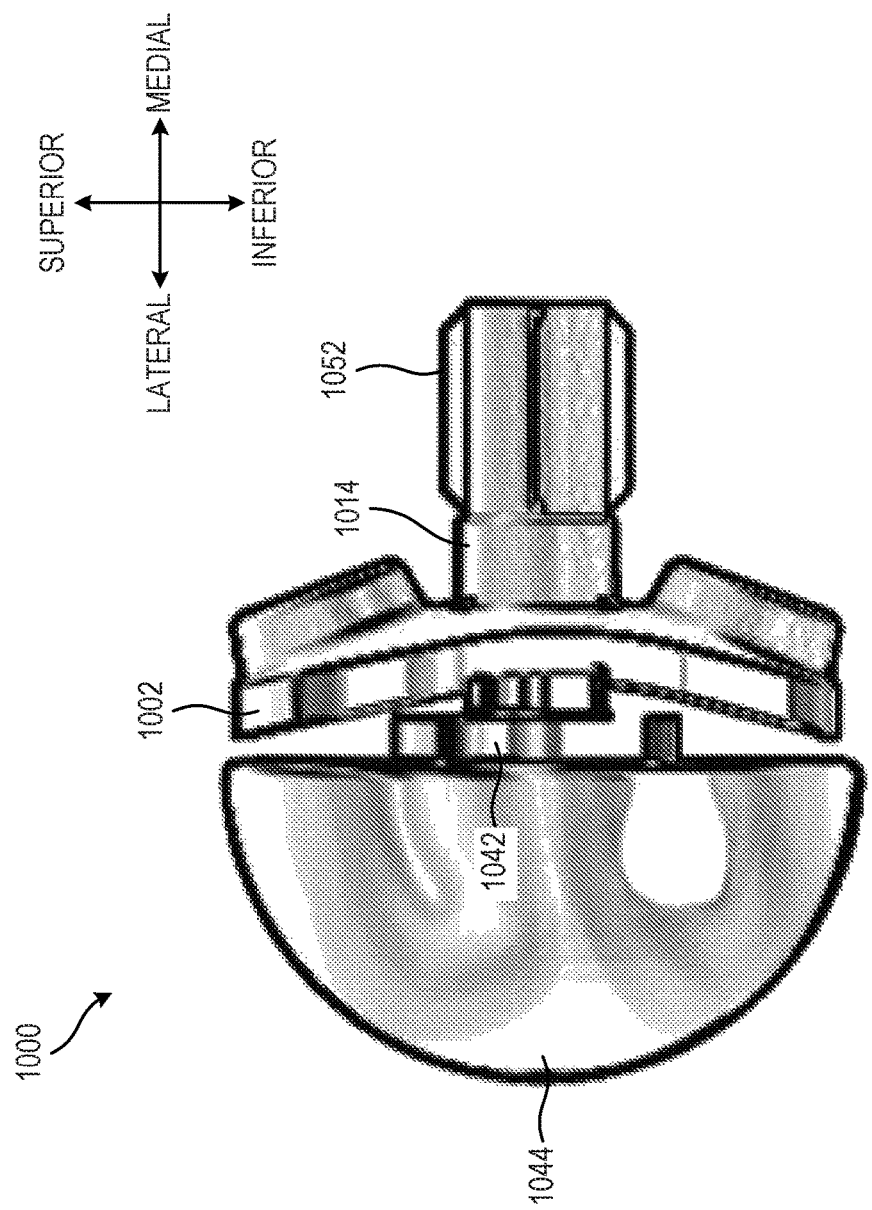
FIG. 10 shows a side view of an example of a glenoid system in the reverse configuration, in accordance with some embodiments.

FIG. 10 shows a side view of an example of a glenoid system 1000 in the reverse configuration, in accordance with some embodiments. Glenoid system 1000 can include a baseplate 1002, an adapter 1042 configured to be attached to a lateral side of the baseplate 1002, a glenosphere 1044 configured to be attached to a lateral side of the adapter 1042, a middle peg 1014 extending medially from the baseplate 1002, and an optional middle peg extension 1052 configured to be screwed onto a medial end of the middle peg 1014.

Figure 11:
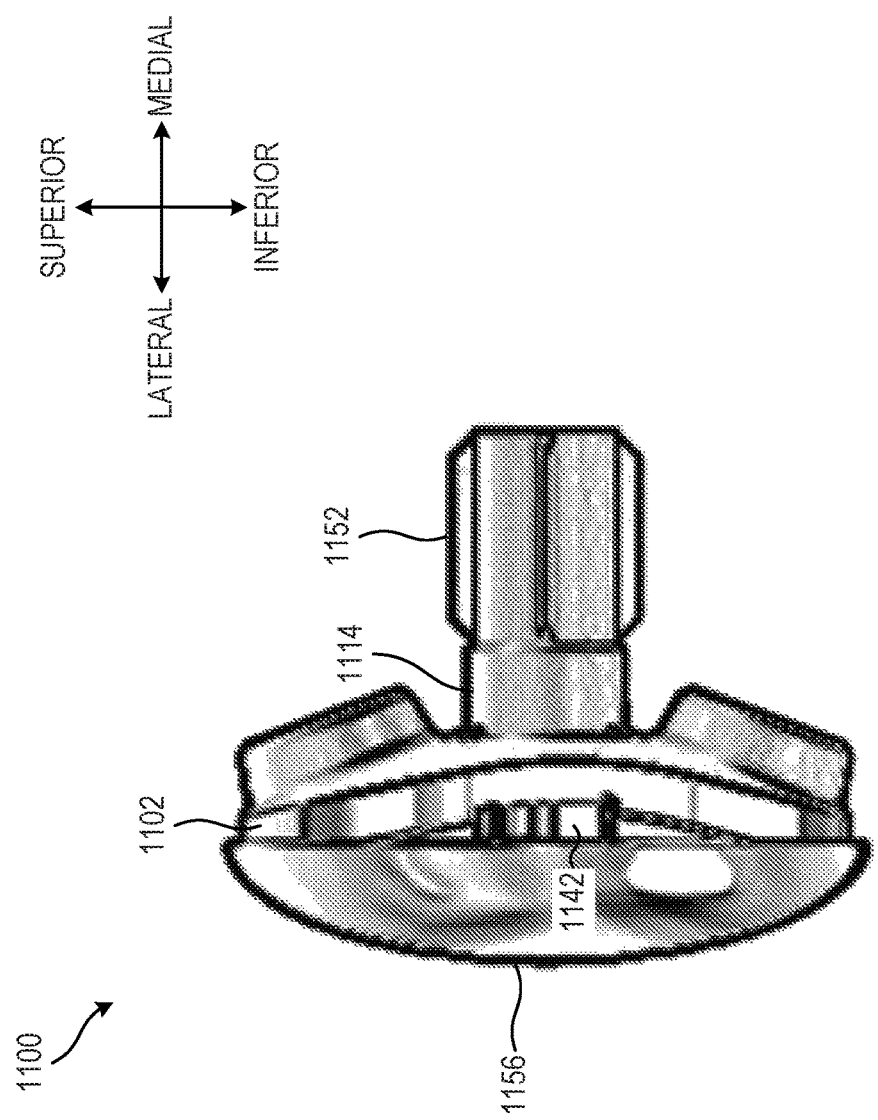
FIG. 11 shows a side view of an example of a glenoid system in a mobile bearing configuration, in accordance with some embodiments.

FIG. 11 shows a side view of an example of a glenoid system 1100 in a mobile bearing configuration, in accordance with some embodiments. The mobile bearing configuration can have the same concavity of the reverse configuration (FIG. 10), but using a relatively shallow glenoid shield 1156 instead of a glenosphere. Glenoid system 1100 can include a baseplate 1102, an adapter 1142 configured to be attached to a lateral side of the baseplate 1102, a glenoid shield 1156 configured to be attached to a lateral side of the adapter 1142, a middle peg 1114 extending medially from the baseplate 1102, and an optional middle peg extension 1152 configured to be screwed onto a medial end of the middle peg 1114.

Figure 12:
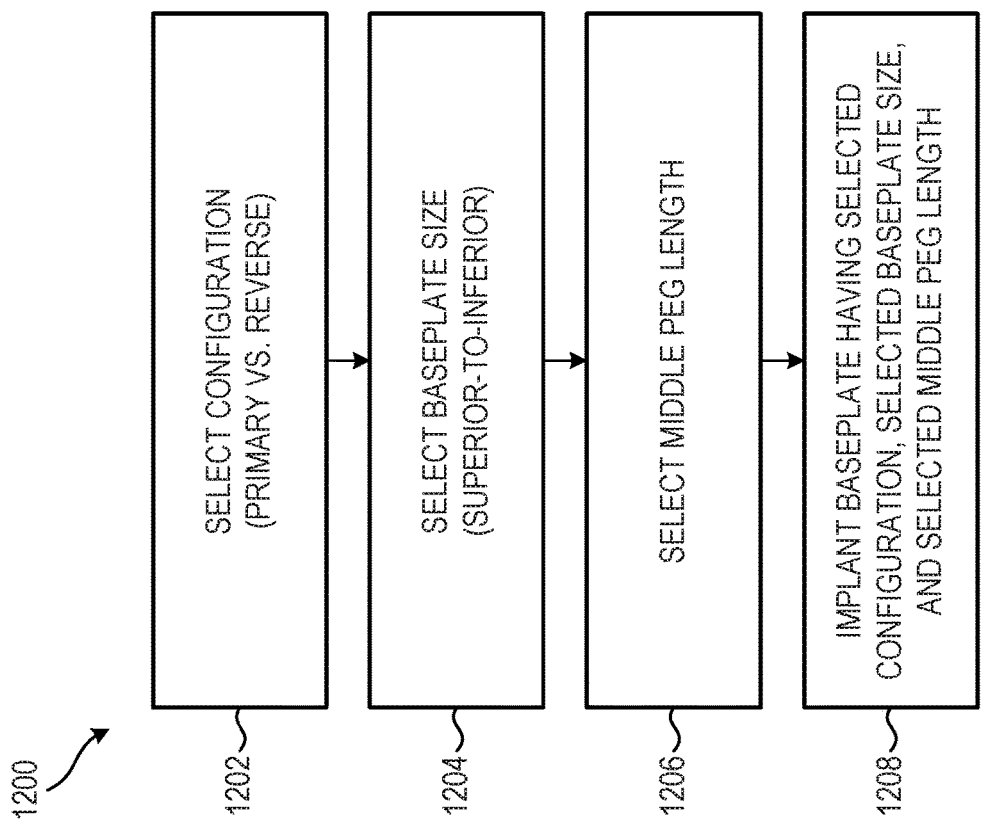
FIG. 12 is a flow chart of an example of a method for implanting a glenoid system, in accordance with some embodiments.

FIG. 12 shows an example of a flow chart of a method 1200 for implanting a glenoid system, such as 100 (FIG. 1), 900 (FIG. 9), 1000 (FIG. 10), 1100 (FIG. 11), or others. The method can be executed by a practitioner, when planning for an operation and operating on a patient.

At operation 1202, the practitioner can select a configuration for the implant. The configurations can include primary or reverse. The selection can depend on the anatomy of the patient, and the reasons for performing the shoulder replacement surgery.

At operation 1204, the practitioner can select a super-to-inferior baseplate size, from a plurality of discrete sizes, which most closely matches an anatomy of the patient.

At operation 1206, the practitioner can select a length for the middle peg, from a plurality of available peg lengths. The available peg lengths can include a fixed length for a middle peg, plus a plurality of discrete lengths for a middle peg extension.

At operation 1208, the practitioner can implant a baseplate, with the selected size, with the selected configuration, and with the selected middle peg length.

The following non-limiting list of examples can further illustrate the present glenoid system.

In Example 1, a glenoid system can include a baseplate configured to attach to a glenoid cavity of a patient. The baseplate can define a lateral-facing surface extending from a superior end of the baseplate to an inferior end of the baseplate. The lateral-facing surface can face laterally when the baseplate is attached to the glenoid cavity. The baseplate can define a superior hole through the lateral-facing surface proximate the superior end of the baseplate. The baseplate can define an inferior hole through the lateral-facing surface proximate the inferior end of the baseplate. The baseplate can define a circumferential edge around at least a portion of the lateral-facing surface. The circumferential edge defining a circumferential groove therein.

In Example 2, the glenoid system of Example 1 can optionally further include a biocompatible plastic liner shaped to snap into the circumferential groove of the baseplate and thereby attach to the baseplate, the biocompatible plastic liner at least partially covering the lateral-facing surface of the baseplate when attached to the baseplate.

In Example 3, the glenoid system of Example 2 can optionally further include wherein the biocompatible plastic liner includes a flexible raised lip around at least a portion of its circumference, the flexible raised lip being configured to deflect radially outward, engage the circumferential groove, and retract radially into the circumferential groove when the biocompatible plastic liner is forced against the baseplate.

In Example 4, the glenoid system of any one of Examples 2-3 can optionally further include wherein the biocompatible plastic liner includes a first smooth face configured to be oriented toward the baseplate and a second smooth face configured to be oriented away from the baseplate.

In Example 5, the glenoid system of any one of Examples 2-4 can optionally further include wherein the biocompatible plastic liner includes a centering feature, the centering feature extending through the baseplate when the biocompatible plastic liner is attached to the baseplate.

In Example 6, the glenoid system of any one of Examples 1-5 can optionally further include wherein the baseplate is coupled to a middle peg at a middle area between the inferior and superior holes, the middle peg extending medially from the baseplate when the baseplate is attached to the glenoid cavity.

In Example 7, the glenoid system of Example 6 can optionally further include wherein the centering feature is configured to extend into a recess in the middle peg, the centering feature forming a non-taper taper fit with the recess in the middle peg.

In Example 8, the glenoid system of any one of Examples 6-7 can optionally further include wherein the middle peg includes a threaded surface configured to mate with a corresponding threaded surface on a middle peg extension.

In Example 9, the glenoid system of any one of Examples 6-7 can optionally further include wherein the middle peg includes a taper configured to form a taper fit with a corresponding taper on a middle peg extension.

In Example 10, the glenoid system of any one of Examples 5-9 can optionally further include wherein the centering feature has an elongated cross-section.

In Example 11, the glenoid system of any one of Examples 1-10 can optionally further include wherein the baseplate is formed from a biocompatible metal or a biocompatible metal alloy.

In Example 12, the glenoid system of any one of Examples 1-11 can optionally further include wherein the lateral-facing surface is concave.

In Example 13, the glenoid system of any one of Examples 1-5 or 11-12 can optionally further include wherein the baseplate is coupled to a middle peg at a middle area between the inferior and superior holes, the middle peg extending medially from the baseplate when the baseplate is attached to the glenoid cavity; and further comprising: an adapter having a first taper, the first taper being a male taper sized and shaped to form a taper fit with a recess in the middle peg, the adapter further having a second taper offset from the first taper, and the second taper being size and shaped to form a taper fit with a glenosphere or a glenoid shield.

In Example 14, the glenoid system of any one of Examples 1-5 or 11-12 can optionally further include wherein the baseplate is coupled to a middle peg at a middle area between the inferior and superior holes, the middle peg extending medially from the baseplate when the baseplate is attached to the glenoid cavity, the baseplate defining a first slot through the lateral-facing surface, and the first slot being elongated circumferentially around the middle area and adjacent to the middle peg.

In Example 15, the glenoid system of any one of Examples 1-5 or 11-12 can optionally further include wherein the baseplate is coupled to a middle peg at a middle area between the inferior and superior holes, the middle peg extending medially from the baseplate when the baseplate is attached to the glenoid cavity, and the middle peg configured to attach to a middle peg extension.

In Example 16, a glenoid system can include a baseplate configured to attach to a glenoid cavity of a patient, the baseplate defining a lateral-facing surface extending from a superior end of the baseplate to an inferior end of the baseplate, the lateral-facing surface facing laterally when the baseplate is attached to the glenoid cavity, the baseplate defining a superior hole through the lateral-facing surface proximate the superior end of the baseplate, the baseplate defining an inferior hole through the lateral-facing surface proximate the inferior end of the baseplate, the baseplate defining a circumferential edge around at least a portion of the lateral-facing surface, and the circumferential edge defining a circumferential groove therein; and a biocompatible plastic liner shaped to snap into the circumferential groove of the baseplate and thereby attach to the baseplate, the biocompatible plastic liner at least partially covering the lateral-facing surface of the baseplate when attached to the baseplate, the biocompatible plastic liner including a flexible raised lip around at least a portion of a circumference of the biocompatible plastic liner, the flexible raised lip being configured to deflect radially outward, engage the circumferential groove, and retract radially into the circumferential groove when the biocompatible plastic liner is forced against the baseplate, the biocompatible plastic liner including a centering feature, and the centering feature extending through the baseplate when the biocompatible plastic liner is attached to the baseplate.

In Example 17, the glenoid system of Example 16 can optionally further include wherein the baseplate is coupled to a middle peg at a middle area between the inferior and superior holes, the middle peg extending medially from the baseplate when the baseplate is attached to the glenoid cavity.

In Example 18, the glenoid system of any one of Examples 16-17 can optionally further include wherein the centering feature is configured to extend into a recess in the middle peg, the centering feature forming a non-taper taper fit with the recess in the middle peg.

In Example 19, a glenoid system can include: a baseplate configured to attach to a glenoid cavity of a patient, the baseplate defining a lateral-facing surface extending from a superior end of the baseplate to an inferior end of the baseplate, the lateral-facing surface facing laterally when the baseplate is attached to the glenoid cavity, the baseplate defining a superior hole through the lateral-facing surface proximate the superior end of the baseplate, the baseplate defining an inferior hole through the lateral-facing surface proximate the inferior end of the baseplate, the baseplate defining a circumferential edge around at least a portion of the lateral-facing surface, and the circumferential edge defining a circumferential groove therein; and a biocompatible plastic liner shaped to snap into the circumferential groove of the baseplate and thereby attach to the baseplate, the biocompatible plastic liner at least partially covering the lateral-facing surface of the baseplate when attached to the baseplate, the biocompatible plastic liner including a flexible raised lip around at least a portion of a circumference of the biocompatible plastic liner, the flexible raised lip being configured to deflect radially outward, engage the circumferential groove, and retract radially into the circumferential groove when the biocompatible plastic liner is forced against the baseplate, the biocompatible plastic liner including a centering feature having an elongated cross-section, and the centering feature extending through the baseplate when the biocompatible plastic liner is attached to the baseplate.

In Example 20, the glenoid system of Example 19 can optionally further include wherein the lateral-facing surface is concave.

The above Detailed Description includes references to the accompanying drawings, which form a part of the Detailed Description. The drawings show, by way of illustration, specific embodiments in which the invention can be practiced. These embodiments are also referred to herein as "examples." Such examples can include elements in addition to those shown or described. However, the inventors also contemplate examples in which only those elements shown or described are provided. Moreover, the inventors also contemplate examples using any combination or permutation of those elements shown or described (or one or more aspects thereof), either with respect to a particular example (or one or more aspects thereof), or with respect to other examples (or one or more aspects thereof) shown or described herein. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, kit, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in The claimed invention is:

1. A glenoid system, comprising:
a baseplate configured to attach to a glenoid cavity of a patient,
the baseplate defining a lateral-facing surface extending from a superior end of the baseplate to an inferior end of the baseplate, the lateral-facing surface facing laterally when the baseplate is attached to the glenoid cavity,
the baseplate defining a superior hole through the lateral-facing surface proximate the superior end of the baseplate,
the baseplate defining an inferior hole through the lateral-facing surface proximate the inferior end of the baseplate,
the baseplate defining a circumferential edge around at least a portion of the lateral-facing surface,
the circumferential edge defining a circumferential groove therein; and
a biocompatible plastic liner shaped to snap into the circumferential groove of the baseplate and thereby attach to the baseplate,
the biocompatible plastic liner at least partially covering the lateral-facing surface of the baseplate when attached to the baseplate,
the biocompatible plastic liner including a flexible raised lip around at least a portion of its circumference,
the flexible raised lip being configured to deflect radially outward, engage the circumferential groove, and retract radially into the circumferential groove when the biocompatible plastic liner is forced against the baseplate.

2. The glenoid system of claim 1, wherein the biocompatible plastic liner includes a first smooth face configured to be oriented toward the baseplate and a second smooth face configured to be oriented away from the baseplate.

3. The glenoid system of claim 1, wherein the biocompatible plastic liner includes a centering feature, the centering feature extending through the baseplate when the biocompatible plastic liner is attached to the baseplate.

4. The glenoid system of claim 3, wherein the baseplate is coupled to a middle peg at a middle area between the inferior and superior holes, the middle peg extending medially from the baseplate when the baseplate is attached to the glenoid cavity.

5. The glenoid system of claim 4, wherein the centering feature is configured to extend into a recess in the middle peg, the centering feature forming a non-taper taper fit with the recess in the middle peg.

6. The glenoid system of claim 4, wherein the middle peg includes a threaded surface configured to mate with a corresponding threaded surface on a middle peg extension.

7. The glenoid system of claim 4, wherein the middle peg includes a taper configured to form a taper fit with a corresponding taper on a middle peg extension.

8. The glenoid system of claim 3, wherein the centering feature has an elongated cross-section.

9. The glenoid system of claim 1, wherein the baseplate is formed from a biocompatible metal or a biocompatible metal alloy.

10. The glenoid system of claim 1, wherein the lateral-facing surface is concave.

11. A glenoid system, comprising:
a baseplate configured to attach to a glenoid cavity of a patient,
the baseplate defining a lateral-facing surface extending from a superior end of the baseplate to an inferior end of the baseplate, the lateral-facing surface facing laterally when the baseplate is attached to the glenoid cavity,
the baseplate defining a superior hole through the lateral-facing surface proximate the superior end of the baseplate,
the baseplate defining an inferior hole through the lateral-facing surface proximate the inferior end of the baseplate,
the baseplate defining a circumferential edge around at least a portion of the lateral-facing surface, the circumferential edge defining a circumferential groove therein,
wherein the baseplate is coupled to a middle peg at a middle area between the inferior and superior holes, the middle peg extending medially from the baseplate when the baseplate is attached to the glenoid cavity,
the baseplate defining a first slot through the lateral-facing surface,
the first slot being elongated circumferentially around the middle area and adjacent to the middle peg.

12. The glenoid system of claim 1,
wherein the baseplate is coupled to a middle peg at a middle area between the inferior and superior holes, the middle peg extending medially from the baseplate when the baseplate is attached to the glenoid cavity, and
the middle peg configured to attach to a middle peg extension.

13. A glenoid system, comprising:
a baseplate configured to attach to a glenoid cavity of a patient,
the baseplate defining a lateral-facing surface extending from a superior end of the baseplate to an inferior end of the baseplate, the lateral-facing surface facing laterally when the baseplate is attached to the glenoid cavity,
the baseplate defining a superior hole through the lateral-facing surface proximate the superior end of the baseplate,
the baseplate defining an inferior hole through the lateral-facing surface proximate the inferior end of the baseplate,
the baseplate defining a circumferential edge around at least a portion of the lateral-facing surface, the circumferential edge defining a circumferential groove therein,
wherein the baseplate is coupled to a middle peg at a middle area between the inferior and superior holes, the middle peg extending medially from the baseplate when the baseplate is attached to the glenoid cavity; and
an adapter having a first taper,
the first taper being a male taper sized and shaped to form a taper fit with a recess in the middle peg,
the adapter further having a second taper offset from the first taper,
the second taper being size and shaped to form a taper fit with a glenosphere or a glenoid shield.

14. A glenoid system, comprising:
a baseplate configured to attach to a glenoid cavity of a patient, the baseplate defining a lateral-facing surface extending from a superior end of the baseplate to an inferior end of the baseplate, the lateral-facing surface facing laterally when the baseplate is attached to the glenoid cavity, the baseplate defining a superior hole through the lateral-facing surface proximate the superior end of the baseplate, the baseplate defining an inferior hole through the lateral-facing surface proximate the inferior end of the baseplate, the baseplate defining a circumferential edge around at least a portion of the lateral-facing surface, the circumferential edge defining a circumferential groove therein; and a biocompatible plastic liner shaped to snap into the circumferential groove of the baseplate and thereby attach to the baseplate, the biocompatible plastic liner at least partially covering the lateral-facing surface of the baseplate when attached to the baseplate, the biocompatible plastic liner including a flexible raised lip around at least a portion of a circumference of the biocompatible plastic liner, the flexible raised lip being configured to deflect radially outward, engage the circumferential groove, and retract radially into the circumferential groove when the biocompatible plastic liner is forced against the baseplate, the biocompatible plastic liner including a centering feature, the centering feature extending through the baseplate when the biocompatible plastic liner is attached to the baseplate.

15. The glenoid system of claim 14, wherein the baseplate is coupled to a middle peg at a middle area between the inferior and superior holes, the middle peg extending medially from the baseplate when the baseplate is attached to the glenoid cavity.

16. The glenoid system of claim 14, wherein the centering feature is configured to extend into a recess in the middle peg, the centering feature forming a non-taper taper fit with the recess in the middle peg.

17. A glenoid system, comprising:

a baseplate configured to attach to a glenoid cavity of a patient, the baseplate defining a lateral-facing surface extending from a superior end of the baseplate to an inferior end of the baseplate, the lateral-facing surface facing laterally when the baseplate is attached to the glenoid cavity, the baseplate defining a superior hole through the lateral-facing surface proximate the superior end of the baseplate, the baseplate defining an inferior hole through the lateral-facing surface proximate the inferior end of the baseplate, the baseplate defining a circumferential edge around at least a portion of the lateral-facing surface, the circumferential edge defining a circumferential groove therein; and a biocompatible plastic liner shaped to snap into the circumferential groove of the baseplate and thereby attach to the baseplate, the biocompatible plastic liner at least partially covering the lateral-facing surface of the baseplate when attached to the baseplate, the biocompatible plastic liner including a flexible raised lip around at least a portion of a circumference of the biocompatible plastic liner, the flexible raised lip being configured to deflect radially outward, engage the circumferential groove, and retract radially into the circumferential groove when the biocompatible plastic liner is forced against the baseplate, the biocompatible plastic liner including a centering feature having an elongated cross-section, the centering feature extending through the baseplate when the biocompatible plastic liner is attached to the baseplate.

18. The glenoid system of claim 17, wherein the lateral-facing surface is concave.

* * * * *